US006653450B1

(12) United States Patent
Berg et al.

(10) Patent No.: US 6,653,450 B1
(45) Date of Patent: Nov. 25, 2003

(54) MUTATED RECOMBINANT COLLAGENS

(75) Inventors: Richard A. Berg, Los Altos, CA (US); Paul David Toman, Palo Alto, CA (US); Donald G. Wallace, Menlo Park, CA (US)

(73) Assignee: Cohesion Technologies, Inc., Palo Alto, CA (US)

( * ) Notice: Subject to any disclaimer, the term of this patent is extended or adjusted under 35 U.S.C. 154(b) by 0 days.

(21) Appl. No.: 08/278,774

(22) Filed: Jul. 22, 1994

Related U.S. Application Data

(63) Continuation-in-part of application No. 08/183,648, filed on Jan. 18, 1994, now Pat. No. 5,662,839, which is a continuation-in-part of application No. 08/011,643, filed on Jan. 28, 1993, now abandoned.

(51) Int. Cl.$^7$ .......................... C07K 14/00; C12P 21/02
(52) U.S. Cl. ...................................... 530/356; 435/69.7
(58) Field of Search ........................ 530/356; 435/69.1, 435/69.7

(56) References Cited

U.S. PATENT DOCUMENTS 5,002,071 A    3/1991    Harrell ....................... 128/897

FOREIGN PATENT DOCUMENTS

WO          WO 8912678         12/1989

OTHER PUBLICATIONS

Chu, M.L., et al. (1984) Nature 310, 337–340.*
Prockop, D.J., et al. (1979) New England Journal Of Medicine 301(1), 13–23.*
Olsen, B.R., et al. (1977) Biochemistry 16(13), 3030–3036.*
S.L. Adams, "Collagen Gene Expression", *American Journal of Respiratory Cell and Molecular Biology,* vol. 1, pp. 1:61–168, (1989).
R. Mayne et al., "New Members of the Collagen Superfamily", *Current Opinion in Cell Biology,* 5:883–890, (1993).
M. Vander Rest et al., "Collagens: Diversity at the Molecular and Supramolecular Levels", *Current Opinion in Structural Biology,* 3:430–436, (1993).
D. Prockop et al., "Heritable Diseases of Collagen", *The New England Journal of Medicine,* 3111:376–386, (1984).
S. T. Lee, "Deletion of the Pro–1(I) N–Propeptide Affects Secretion of Type I Collagen in Chinese Hamster Lung Cells But Not in Nov–13 Mouse", *Journal of Biological Chemistry,* 267:24126–24133, (1992).
Paul Carter, "Molecular Mechanisms to Large–Scale Processes: Site–Specific Proteolysis of Fusion Proteins", *American Chemical Society Research Symposium,* 47:181–193, (1990).
C. Brenner et al., "Structural and Enzymatic Characterization of a Purified Prohormone–Processing Enzyme: Secreted, Soluble Kex2 Protease", *Proc.Natl. Acad. Sci.,* 89:922–926, (1992).

P. Seeboth et al., "In–vitro Cleavge of a Fusion Protein Bound to Cellulose Using the Soluble yscFs (Kex2) Variant", *Appl. Microbiotechnol,* 37:621–625, (1992).
A. Fontana et al., *Practical Protein Chemistry–A Handbook,* Chap. 2, pp. 66–120, Darby Ed., John Wiley and Sons: London (1986).
Y. Saito et al., "Production and Isolation of Recombinant Somatomedin C", *J. Biochem,* 101:123–134, (1987).
E. Miller et al., "Preparation and Characterization of the Different Types of Collagen", *Methods in Enzymology,* vol. 82, pp. 33–64, (1982).
H. Sage et al., "Preparation and Characterization of Procollagens and Procollagen–Collagen Intermediates", *Methods in Enzymology,* vol. 82, pp. 96–127, (1982).
A. Stacey et al., "Rescue of Type I Collagen–Deficient Phenotype by Retroviral–Vector–Mediated Transfer of Human Pro 1(I) Collagen Gene into Mov–13 Cells", *Journal of Virology,* vol. 61, No. 8, pp. 2549–2554, (1987).
G. Tromp et al., "Structure of a Full–Length cDNA Clone for the Preprox 1(I) Chain of Human Type I Procollagen", *Biochem J.,* 253:919–922, (1988).
S.T. Lee et al., "Construction of a Full–Length cDNA Encoding Human Pro–2(I) Collagen and Its Expression in Pro–2(I) Deficient W8 Rat Cells", *The Journal of Biological Chemistry,* vol. 263, No. 26, pp. 13414–13418, (1988).
L. Dickson et al., "Analysis of the Promoter Region and the N–Propeptide Domain of the Human Pro 2(I) Collagen Gene", *Nucleic Acids Research,* vol. 13, No. 10, pp. 3427–3438 (1985).
E. Ozkaynak et al., "The Yeast Ubiquitin Genes: A Family of Natural Gene Fusions", *The EMBO Journal,* vol. 6, No. 5, pp. 1429–1439, (1987).

(List continued on next page.)

*Primary Examiner*—Charles L. Patterson, Jr.
(74) *Attorney, Agent, or Firm*—Richard Aron Osman (57) ABSTRACT

The invention provides recombinant procollagen chains having a natural collagen chain separated from one or two propeptides by one or two non-natural site-specific proteolytic agent (e.g., protease) recognition sites. A wide variety of propeptides and site-specific proteolytic agent recognition sites may be used: the selection of particular site-specific proteolytic agent/recognition site pairs is based on the conformation of the resulting procollagen, the availability of the site-specific proteolytic agent, the compatibility of the proteolysis with production of mature collagen, among other factors. Recombinant collagens chains are produced by contacting the subject recombinant procollagen chains with the appropriate site-specific proteolytic agents. Nucleic acids encoding the subject procollagen chains operably linked to transcription regulatory elements are used in vectors and cells for the production of recombinant collagen. Such collagen is used in tissue and cell cultureware and therapeutically, such as in biodegradable surgical materials and for tissue augmentation.

2 Claims, 4 Drawing Sheets

OTHER PUBLICATIONS

J. Tobias et al., "Cloning and Functional Analysis of the Ubiquitin–Specific Protease Gene UBP1 of Saccharomyces Cerevisiae", vol. 266, No. 18, pp. 12021–12028, (1991).

J. Han et al., "Isolation of Full–Length Putative Rat Lysophospholipase cDNA Using Improved Methods for mRNA Isolation and cDNA Cloning", *Biochemistry*, vol. 26, pp. 1617–1625, (1987).

Petry et al., "Isolation, Sequence Analysis and Characterization of cDNA Clones Coding for the C Chain of Mouse C1q", *J. Biochem,* vol. 209, pp. 129–134, (1992).

* cited by examiner

```
                          SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
         (A) LENGTH: 4 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:1:

Asp Asp Asp Lys
1

(2) INFORMATION FOR SEQ ID NO:2:

(i) SEQUENCE CHARACTERISTICS:
         (A) LENGTH: 4 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:2:

Ile Glu Gly Arg
1
```

(2) INFORMATION FOR SEQ ID NO:3:

(i) SEQUENCE CHARACTERISTICS:
        (A) LENGTH: 7 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO:3:

```
Tyr Ile His Pro Phe His Leu
1               5
```

(2) INFORMATION FOR SEQ ID NO:4:

(i) SEQUENCE CHARACTERISTICS:
        (A) LENGTH: 4 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO:4:

```
Ala Ala His Tyr
1
```

(2) INFORMATION FOR SEQ ID NO:5:

(i) SEQUENCE CHARACTERISTICS:
        (A) LENGTH: 4 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO:5:

```
Arg Gly Pro Arg
1
```

(2) INFORMATION FOR SEQ ID NO:6:

(i) SEQUENCE CHARACTERISTICS:
        (A) LENGTH: 17 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO:6:

```
Gln Leu Ser Tyr Gly Tyr Asp Glu Lys Ser Thr Gly Gly Ile Ser Val
1               5                   10                  15
Pro
```

(2) INFORMATION FOR SEQ ID NO:7:

(i) SEQUENCE CHARACTERISTICS:
        (A) LENGTH: 15 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO:7:

```
Pro Gly Pro Pro Gly Pro Pro Gly Leu Gly Gly Asn Phe Ala Pro
1               5                   10                  15
```

(2) INFORMATION FOR SEQ ID NO:8:

(i) SEQUENCE CHARACTERISTICS:
        (A) LENGTH: 15 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO:8:

```
Pro Pro Gln Glu Lys Ala His Asp Gly Gly Arg Tyr Tyr Arg Ala
1               5                   10                  15
```

(2) INFORMATION FOR SEQ ID NO:9:

(i) SEQUENCE CHARACTERISTICS:
        (A) LENGTH: 15 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO:9:

```
Asp Asp Ala Asn Val Val Arg Asp Arg Asp Leu Glu Val Asp Thr
1               5                   10                  15
```

(2) INFORMATION FOR SEQ ID NO:10:

(i) SEQUENCE CHARACTERISTICS:
        (A) LENGTH: 11 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO:10:

```
Gln Tyr Asp Gly Lys Gly Val Gly Leu Gly Pro
1               5                   10
```

(2) INFORMATION FOR SEQ ID NO:11:

(i) SEQUENCE CHARACTERISTICS:
        (A) LENGTH: 15 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO:11:

```
Pro Gly Pro Pro Gly Pro Pro Gly Leu Gly Gly Asn Phe Ala Ala
1               5                   10                  15
```

(2) INFORMATION FOR SEQ ID NO:12:

(i) SEQUENCE CHARACTERISTICS:
        (A) LENGTH: 16 amino acids
        (B) TYPE: amino acid
        (C) STRANDEDNESS: single
        (D) TOPOLOGY: linear     (ii) MOLECULE TYPE: peptide (xi) SEQUENCE DESCRIPTION: SEQ ID NO:12:

Gly Gly Gly Tyr Asp Phe Gly Tyr Asp Gly Asp Phe Tyr Arg Ala Xaa
1               5                   10                  15

(2) INFORMATION FOR SEQ ID NO:13:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Asp Gln Pro Arg Ser Ala Pro Ser Leu Arg Pro Lys Asp Tyr Glu
1               5                   10                  15

(2) INFORMATION FOR SEQ ID NO:14:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Gln Met Ala Gly Gly Phe Asp Glu Lys Ala Gly Gly Ala Gln Met Gly
1               5                   10                  15

Val Gln Met (2) INFORMATION FOR SEQ ID NO:15:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Pro Gly Pro Pro Gly Pro Pro Gly Leu Gly Gly Asn Phe Ala Ala
1               5                   10                  15

(2) INFORMATION FOR SEQ ID NO:16:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Gly Pro Arg Glu Lys Gly Pro Asp Pro Met Gln Tyr Met Arg Ala
1               5                   10                  15

(2) INFORMATION FOR SEQ ID NO:17:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

```
Asp Glu Ala Asp Ser Thr Leu Arg Gln His Asp Val Glu Val Asp
1               5                   10                  15
```

(2) INFORMATION FOR SEQ ID NO:18:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Gln Tyr Asp Ser Tyr Asp Val Lys Ser Gly Val Ala Val Gly
1               5                   10
```

(2) INFORMATION FOR SEQ ID NO:19:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

```
Gly Ile Cys Glu Ser Cys Pro Thr Gly Pro Gln Asn Tyr Ser Pro
1               5                   10                  15
```

(2) INFORMATION FOR SEQ ID NO:20:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

```
Gly Ile Gly Gly Glu Lys Ala Gly Gly Phe Ala Pro Tyr Tyr Gly
1               5                   10                  15
```

(2) INFORMATION FOR SEQ ID NO:21:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

```
Asp Glu Pro Met Asp Phe Lys Ile Asn Thr Asp Glu Ile Met Thr
1               5                   10                  15
```

(2) INFORMATION FOR SEQ ID NO:22:

(i) SEQUENCE CHARACTERISTICS:
        (A) LENGTH: 24 base pairs
        (B) TYPE: nucleic acid
        (C) STRANDEDNESS: single (D) TOPOLOGY: linear (ii) MOLECULE TYPE: cDNA (xi) SEQUENCE DESCRIPTION: SEQ ID NO:22:

ACGCCAAGCT TGGCTGCAGG TCGA                                              24

(2) INFORMATION FOR SEQ ID NO:23:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

CTGTTTATCA TCGTCGGGAG CAAAGTTTCC TCC                                     33

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

GAGTCACCCA CCGACCAAGA                                                   20

(2) INFORMATION FOR SEQ ID NO:25:

(i) SEQUENCE CHARACTERISTICS:
        (A) LENGTH: 109 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:25:

GCTGGTTTCG ACTTCAGCTT CCTCCCCCAG CCACCTCAAG AGAAGGCTCA CGATGGTGGC        60

CGCTACTACC GGGCTTGGGA TGATGCCAAT GTGGTTCGTG ACCGTGACC                   109

(2) INFORMATION FOR SEQ ID NO:26:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

GTGGTATGCA AATTTTTGTC AAGACTTTGA CTG                                     33

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

CCACCTCTCA ATCTCAAGAC T                                                 21

(2) INFORMATION FOR SEQ ID NO:28:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:28:

CCAGTATGAT GGAAAAGGAG TT                                                22

(2) INFORMATION FOR SEQ ID NO:29:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:29:

CGAGCACCTG CAGGACCAGT T                                                 21

(2) INFORMATION FOR SEQ ID NO:30:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:30:

TGGTCCTAGG GGCCCTGCTG GTCCTT                                            26

(2) INFORMATION FOR SEQ ID NO:31:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:31:

TCTACCTTCT ATAGCCCTGT AGAAGTCTCC ATCGTA                                 36

(2) INFORMATION FOR SEQ ID NO:32:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:32:

-continued

```
AAACAGAAGC ACCAGTCGGT ATTCA                                      25

(2) INFORMATION FOR SEQ ID NO:33:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

ATATGAATTC TCAGGTGCAC GCACAGGTTG GCCGTA                           36
```

MUTATED RECOMBINANT COLLAGENS

CROSS-REFERENCES

This application is a continuation-in-part of U.S. application Ser. No. 08/183,648, filed Jan. 18, 1994, now U.S. Pat. No. 5,667,839, which is a continuation-in-part of copending U.S. application Ser. No. 08/011,643, filed Jan. 28, 1993, now abandoned, which applications are incorporated herein by reference in full, and to which we claim priority under 35 U.S.C. §120.

FIELD OF THE INVENTION

The field of this invention is recombinant procollagens containing novel cleavage sites.

BACKGROUND OF THE INVENTION

Collagen has provided a number of commercial applications, including use as a convenient substrate for cell culture, as well as in the manufacture of biocompatible materials (e.g., artificial skin) having a variety of therapeutic applications in humans. Commercially available collagens are primarily isolated from freshly killed farm animals (e.g., cows, pigs, chickens) in polymerized form or in soluble form derived by enzymatic or chemical treatment of polymerized collagen. However, polymerized collagens, and soluble collagens derived from polymerized collagens, are of limited usefulness due to the presence of natural crosslinks within the collagen. Furthermore, non-human collagens can provoke undesirable immune responses when administered to human subjects.

As one alternative, human collagen can be purified from human sources such as human placenta, as described in U.S. Pat. No. 5,002,071 (Research Development Foundation) and in copending U.S. application Ser. No. 07/921,810 (Collagen Corporation). In addition to source limitations and the risk of contamination by human pathogens such as Hepatitis viruses and HIV, the methods for recovering collagen from these sources bias the type of collagen recovered. Furthermore, because the collagen is derived from naturally crosslinked tissues, the collagen recovered is not entirely homogeneous. Another approach to the production of human collagen is the expression of recombinant human collagen in the milk of transgenic animals, as described in copending U.S. applications Ser. Nos. 08/183,648 and 08/011,643 (Collagen Corporation). However, this approach subjects the recombinant collagen to any host deficiencies in translational processing.

The term collagen refers to a type of protein that encompasses a class of structurally related polypeptides consisting of helical collagen chains and homo- and heteromeric polymers thereof. Collagen chains often contain both long helical domains and non-helical extensions, or telopeptides. The helical domains comprise -(GXY)n- repeats, where X and/or Y are frequently proline or hydroxyproline.

Collagen polypeptide chains are encoded by a number of related genes. See S. L. Adams, *Amer. J. Respir. Cell and Mol. Biol.* (1989) 1:161–168; Mayne and Brewton, *Current Opinion in Cell Biology* (1993) 5:883–890; and van der Rest and Bruckner, *Current Opinion in Structural Biology* (1993) 3:430–436. Collagen-encoding transcripts are initially translated into procollagen chains which undergo a variety of post-translational events such as processing, secretion, and assembly (e.g., disulfide exchange, prolyl residue hydroxylation, glycosylation, and crosslinking of the helical chains; see, for example, Prockop et al., *New England J. Med.* (1984) 3111:376–386) to form mature collagen chain helices. In addition, procollagens contain N- and C-terminal propeptides that facilitate collagen formation. See, for example, Lee et al., *J. Biol. Chem.* (1992) 267: 24126–24133.

Many of these post-translational events are catalyzed by enzymes thought to be expressed only in or by cells which naturally produce collagen. For example, the procollagen propeptides are cleaved from the procollagens by tissue-specific procollagen N- and C-terminal proteases. Accordingly, recombinant production of collagen has been severely restricted by the inability of conventional cellular expression systems to efficiently post-translationally modify procollagen to form functionally mature collagen.

Site-specific proteolysis of unrelated fusion proteins is reported by Paul Carter in *Protein Purification: From Molecular Mechanisms to Large-Scale Processes*, American Chemical Society Research Symposium (1990) 47:181–193; Brenner and Fuller, *PNAS* (1992) 89:922–926; Seeboth et al., *Appl. Microbiol. Biotechnol.* (1992) 37:621–625; and Liu and Miller, WO 8912678. Chemical cleavage is described in Chapter 2 of Fontana and Gross, *In Practical Protein Chemistry—A Handbook*, Darby, Ed., John Wiley and Sons, London (1986).

SUMMARY OF THE INVENTION

The invention provides recombinant procollagen chains having a natural collagen polypeptide chain separated from a propeptide by a non-natural site-specific proteolytic agent recognition site (i.e., the site is not naturally present at that location of a natural procollagen chain). The propeptide is often a C-terminal propeptide and, frequently, a natural procollagen C-terminal propeptide. Alternatively, the recombinant procollagen chains may further comprise a second propeptide separated from the opposite end of the natural collagen chain by a second non-natural site-specific proteolytic agent recognition site.

A wide variety of propeptides and site-specific proteolytic agent recognition sites may be used. The propeptide is capable of increasing the yield of at least one of secreted procollagen (trimeric procollagen chains) or collagen monomers (trimeric collagen chains) from cells expressing procollagen chains comprising the propeptide, as compared with cells expressing the same collagen chains alone, without the propeptide. The non-natural site-specific proteolytic agent recognition site is generally selected to provide a substrate for a convenient site-specific proteolytic agent. The agent is commonly a protease or a chemical agent which selectively cleaves at accessible and preferentially labile peptide bonds. Where two site-specific proteolytic agent recognition sites and two propeptides are present, the recognition sites may have the same or different amino acid sequences, with the same or different site-specific proteolytic agent affinities and specificities.

The subject procollagen chains may be constructed such that the site-specific proteolytic agent cleavage site is a peptide bond that separates the collagen chain and/or the propeptide from the remainder of the procollagen chain. Alternatively, the cleavage site may be a peptide bond that separates, from the remainder of the procollagen chain, the collagen chain (or propeptide), joined to at least one amino acid which is not naturally present at that location of a natural collagen chain (or propeptide).

The invention provides collagens produced by contacting the subject recombinant procollagen with site-specific proteolytic agents capable of selectively cleaving the procollagen chains at the site-specific proteolytic agent recognition sites, wherein the resulting chains comprise terminal peptides which may have non-natural amino acid sequences (i.e., not naturally present at that location of a natural collagen chain). The resulting collagen may be employed directly (e.g. to coat cell culture dishes or cultureware) or further polymerized and/or provided in sterile, nontoxic, biocompatible collagen compositions suitable for administration to humans.

The invention also provides nucleic acids encoding the subject procollagen chains, as well as vectors and cells comprising such nucleic acids operably linked to transcription regulatory elements not naturally linked to such nucleic acids. The invention provides processes for the production of recombinant procollagen and/or collagen chains in and from such cells. The invention also provides methods of utilizing the resulting procollagen and collagen, for example, coating cultureware and augmenting localized tissue in a host by, for example, subcutaneous administration.

DETAILED DESCRIPTION OF THE PREFERRED EMBODIMENTS OF THE INVENTION

The invention provides recombinant procollagen chains comprising a natural collagen chain, a propeptide, and a non-natural site-specific proteolytic agent recognition site (i.e., not naturally present at that location of a natural collagen chain) located between the collagen chain and the propeptides.

The propeptide increases the yield of at least one of secreted procollagen (trimeric procollagen chains) or collagen monomers (trimeric collagen chains) recoverable from cells expressing the subject recombinant procollagen chains, as compared with cells expressing the collagen chains alone, without the propeptide. Generally, the yield is enhanced by at least 50%, preferably at least about 100%, more preferably at least about 200%, and most preferably at least about 1,000% in at least one expression system.

Collagen refers to a variety of helical arrays of collagen chains and includes both polymerized and monomeric collagen. The propeptides are believed to improve collagen and/or procollagen yields by facilitating or increasing at least one of proper expression, processing, secretion, or polymerization of the procollagen chain, the collagen chain, and/or a collagen monomer. The function of the propeptide is readily monitored by comparing the yields of recoverable collagen and/or procollagen with and without the presence of the propeptide in in vitro or in vivo expression systems including lysates, transformed or transfected cells (such as mammalian cells or yeast), transgenic animals, etc. Specific examples of assays for propeptides are described below.

The propeptide may take a wide variety of forms and sizes: it may be a natural procollagen propeptide, or a propeptide not naturally present as a propeptide in a procollagen chain, as long as it provides the procollagen with the requisite collagen yield. Generally, propeptides are at least 10, preferably at least about 25, more preferably at least about 75, and most preferably at least about 200 amino acids in length. The propeptide is generally located at the C-terminus or N-terminus of the procollagen chain, or the procollagen chain may have propeptides at both termini. Where the recombinant procollagen chains contain both C- and N-terminal propeptides, the chains often comprise a second (and often non-natural) site-specific proteolytic agent recognition site located between the collagen chain and the second propeptide.

Preferred procollagen chains comprise at least a C-terminal propeptide, frequently a natural C-terminal portion of a protein with collagen-like repeats and/or a helical, especially triple-helical, polymeric form, such as complement protein Clq-C, acetocholine esterase, or lung surfactant protein. Especially preferred are natural procollagen C-terminal propeptides, such as collagen Type I, II, III, IV, V, and XI C-terminal propeptides. Preferred N-terminal propeptides comprise at least one globular domain and often consist essentially of a single globular domain. Especially preferred are natural procollagen N-terminal propeptides, such as collagen type I, II, III, IV, V, and XI N-terminal propeptides.

After cleavage from the collagen chain, the propeptides are preferably purified out of the collagen composition. The propeptides are preferably selected such that, if small quantities of the propeptides remain in the collagen composition after processing, the residual propeptides do not interfere with the intended application of the resulting composition. For example, for in vivo use, the composition should not contain contaminants present in an amount sufficient to cause a toxic or immunogenic response or reaction in the patient.

A wide variety of site-specific proteolytic agent recognition sites may be used. The recognition site is non-natural to a natural procollagen chain, meaning that the site occupies a portion of the procollagen chain not naturally occupied by the recognition site. Frequently, the site is not naturally present anywhere in the natural counterpart of the procollagen chain. The site generally comprises one or more amino acid residues or derivatives thereof. The recognition site may comprise a modified (e.g., methylated) residue, especially for some chemical proteolytic agents. These sites are selected to provide substrates for at least one convenient site-specific proteolytic agent, preferably a commercially available site-specific proteolytic agent. The precise site selection will depend on the selected expression system, the selected propeptide, and the availability of the site-specific proteolytic agent. For example, the site should provide a highly selective target for the selected site-specific proteolytic agent, such that the target site (or both target sites) is cleaved while minimizing hydrolysis of peptide bonds within the collagen chain.

A large number of site-specific proteolytic agents and their recognition sites are known and/or commercially available. See, for example, Carter (1990, supra); Saito et al., *J. Biochem.* (1987) 101:123–134; etc. For example, a wide variety of chemical cleavage agents and their recognition sites are known, e.g., hydroxylamine: N↓G; formic acid: D↓P; acetic acid: D↓P; cyanogen bromide: M↓; BNPS-skatole: W↓; o-iodosobenzoic acid: W↓; N-chlorosuccinimide: W↓; etc. Alternatively, natural or synthetic proteases (e.g., catalytic antibodies, etc.) may be used. Examples of proteases and their recognition sites include: chymotrypsin: W↓ and Y↓ and F↓; collagenase: P-X↓G-P; endoproteinase Lys-C: K↓; enterokinase: D-D-D-K↓ (SEQ ID NO:1:); Factor $X_a$: I-E-G-R↓ (SEQ ID NO:2:); kallikrein: P-F-R↓; renin: Y-I-H-P-F-H-L↓L (SEQ ID NO:3:); H64A subtilisin BPN: A-A-H-Y↓ (SEQ ID NO:4:); thrombin: R-G-P-R↓ (SEQ ID NO:5:); trypsin: R↓ and K↓; ubiquitin protein peptidase: ubiquitin↓; etc. A wide variety of methods may be used to increase the efficiency of cleavage at a target site (e.g., the provision of flanking poly-glycine peptides to enhance accessibility) and/or to reduce non-target site cleavage (e.g., optimizing concentration ratios and reaction conditions).

Preferred site/site-specific proteolytic agent combinations yield a collagen product that is conveniently adapted to the ultimate intended application. For example, any residual non-natural terminal residues should not interfere with and, preferably, enhance the performance (e.g., the promotion of cell growth or adherence to coated cultureware) of the resulting collagen product vis-a-vis the natural collagen counterpart. For in vivo use, the resulting collagen should not be immunologically reactive in the host from which the collagen chain is derived. Generally, immunological non-reactivity is effected by minimizing the number of non-collagen chain amino acid residues which remain joined to the collagen chain after site-specific proteolytic agent cleavage. Preferred site/site-specific proteolytic agent combinations yield collagen chains with fewer than 75, preferably fewer than 25, more preferably fewer than 10, most preferably fewer than 5 and, especially, zero, non-natural collagen chain terminal amino acid residues. Hence, preferred sites and site-specific proteolytic agents provide cleavage at or near the junction with natural collagen chain residues.

Where two site-specific proteolytic agent recognition sites and two propeptides are present, the site-specific proteolytic agent recognition sites may have the same or different amino acid sequences, with the same or different site-specific proteolytic agent affinities and specificities. The site-specific proteolytic agent recognition site(s) generally, but need not, abut both the collagen chain and respective propeptide; i.e., the subject procollagen chains may also have a natural or non-natural (i.e., not naturally present at that location of a natural procollagen chain) amino acid sequence between the site-specific proteolytic agent recognition site and the collagen chain, and/or between the site-specific proteolytic agent recognition site and the propeptide. Accordingly, depending on the selected recognition site, site-specific proteolytic agent, and presence or absence of residues separating the cleavage site from the collagen chain, the resulting (after cleavage) recombinant collagen chains may comprise one or both terminal peptides having a non-natural amino acid sequence. By way of example:

for human α1(I) collagen, a preferred N-terminal peptide is $NH_2$-$X_1X_2X_3X_4X_5X_6X_7X_8X_9X_{10}X_{11}X_{12}X_{13}X_{14}X_{15}$ QLSYGYDEKSTGGISVP (SEQ ID NO:6:), where "$X_1$–$X_{15}$" is other than PGPPGPPGLGGNFAP (SEQ ID NO:7:); and a preferred C-terminal peptide is PPQEKAHDGGRYYRA (SEQ ID NO:8:) $X_1X_2X_3X_4X_5X6X_7X_8X_9X_{10}X_{11}X_{12}X_{13}X_{14}X_{15}$, where "$X_1$–$X_{15}$" is other than DDANVVRDRDLEVDT (SEQ ID NO:9:);

for human α2(I) collagen, a preferred N-terminal peptide is $NH_2$-$X_1X_2X_3X_4X_5X_6X_7X_8X_9X_{10}X_{11}X_{12}X_{13}X_{14}X_{15}$QY DGKGVGLGP (SEQ ID NO:10:), where "$X_1$–$X_{15}$" is other than PGPPGPPGLGGNFAA (SEQ ID NO:11:); and a preferred C-terminal peptide is GGGYDF-GYDGDFYRA (SEQ ID NO:12:) $X_1X_2X_3X_4X_5X_6X_7X_8X_9X_{10}X_{11}X_{12}X_{13}X_{14}X_{15}$, where "$X_1$–$X_{15}$" is other than DQPRSAPSLRPKDYE (SEQ ID NO:13:);

for human α1(II) collagen, a preferred N-terminal peptide is $NH_2$-$X_1X_2X_3X_4X_5X_6X_7$ba$X_8X_9X_{10}X_{11}X_{12}X_{13}X_{14}X_{15}$QMAGGFDEKAGGAQM GVQM (SEQ ID NO:14:), where "$X_1$–$X_{15}$" is other than PGPPGPPGLGGNFAA (SEQ ID NO:15:); and a preferred C-terminal peptide is GPREKGPDPMQYMRA (SEQ ID NO:16:) $X_1X_2X_3X_4X_5X_6X_7X_8X_9X_{10}X_{11}X_{12}X_{13}X_{14}X_{15}$, where "$X_1$–XI5" is other than DEADSTLRQHDVEVD (SEQ ID NO:17:);

for human α1(III) collagen, a preferred N-terminal peptide is N $H_2$-$X_1X_2X_3X_4X_5X_6X_7X_8X_9X_{10}X_{11}X_{12}X_{13}X_{14}X_{15}$QYDSYDVKSGVAVG (SEQ ID NO:18:), where "$X_1$–$X_{15}$" is other than GICESCPTGPQNYSP (SEQ ID NO:19:); and a preferred C-terminal peptide is GIGGEKAGGFAPYYG (SEQ ID NO:20:) $X_1X_2X_3X_4X_5X_6X_7X_8X_9X_{10}X_{11}X_{12}X_{13}X_{14}X_{15}$, where "$X_1$–$X_{15}$" is other than DEPMDFKINTDEIMT (SEQ ID NO:21:).

The invention provides recombinant collagen chains produced by contacting the subject recombinant procollagen chains with site-specific proteolytic agents capable of selectively cleaving the procollagen chain at site-specific proteolytic agent recognition sites. Useful collagen compositions produced by such methods may retain residual site-specific proteolytic agents, wherein the site-specific proteolytic agents are present at concentrations that may exceed 1 picogram, frequently exceed 1 nanogram, and more frequently exceed 1 microgram per gram of collagen protein. Resulting collagen compositions may be subjected to conditions known in the art to be conducive to higher-order polymerization of the collagen, for example, fibril formation. Monomeric or polymeric collagen compositions may be further subjected to a wide variety of manipulations depending on the intended application. For example, the collagen may be diluted in a solvent for optimal adsorption to solid substrates (e.g., glass or plastics such as polystyrene, polyethylene, polypropylene, acetate, nylon, etc.) useful in tissue or cell culture, or purified and sterilized (e.g., filter sterilization) for use in vivo, such as for tissue augmentation.

The invention provides nucleic acids encoding the subject recombinant procollagen chains. These nucleic acids may have a wide variety of forms and sizes and frequently comprise non-coding sequences which facilitate transcription of the encoded procollagen chains. Constructs comprising such nucleic acids operably linked to transcription regulatory elements are spliced into replication and/or transfection vectors, which are then used to transfect/transform cells.

Nucleic acids encoding the collagen chain portions (e.g., col1A1, col1A2, and col3A1) and the site-specific proteolytic agent recognition portions of the subject nucleic acids are readily available, for example, through published sequences, including electronic databases (e.g., Genbank, the National Center for Biotechnology Information at the National Library for Medicine, etc.), through commercial vendors, through library hybridization with otherwise available collagen-encoding nucleic acids, or through known molecular cloning techniques. Materials and methods for constructing (e.g., recombinantly or synthetically) the subject procollagen-encoding nucleic acids, expression vectors, transformed and transfected cells, processes for producing a recombinant procollagen chain (including selection from a wide variety of cells, e.g., cultured mammalian cells such as fibroblasts, CHO cells, yeast, mammary gland cells of transgenic mammals, etc.), transfecting/transforming and culturing the cells under conditions suitable for the expression of the nucleic acid, and recovering and purifying recombinant procollagen chains are disclosed herein or otherwise known in the art. See, for example, *Molecular Cloning: A Laboratory Manual* (2nd Ed., Sambrook, Fritsch, and Maniatis, Cold Spring Harbor) or *Current Protocols in Molecular Biology* (Eds. Aufubel, Brent, Kingston, More, Feidman, Smith, and Stuhl, Greene Publ. Assoc., Wiley-Interscience, NY, 1992).

Figure 1:
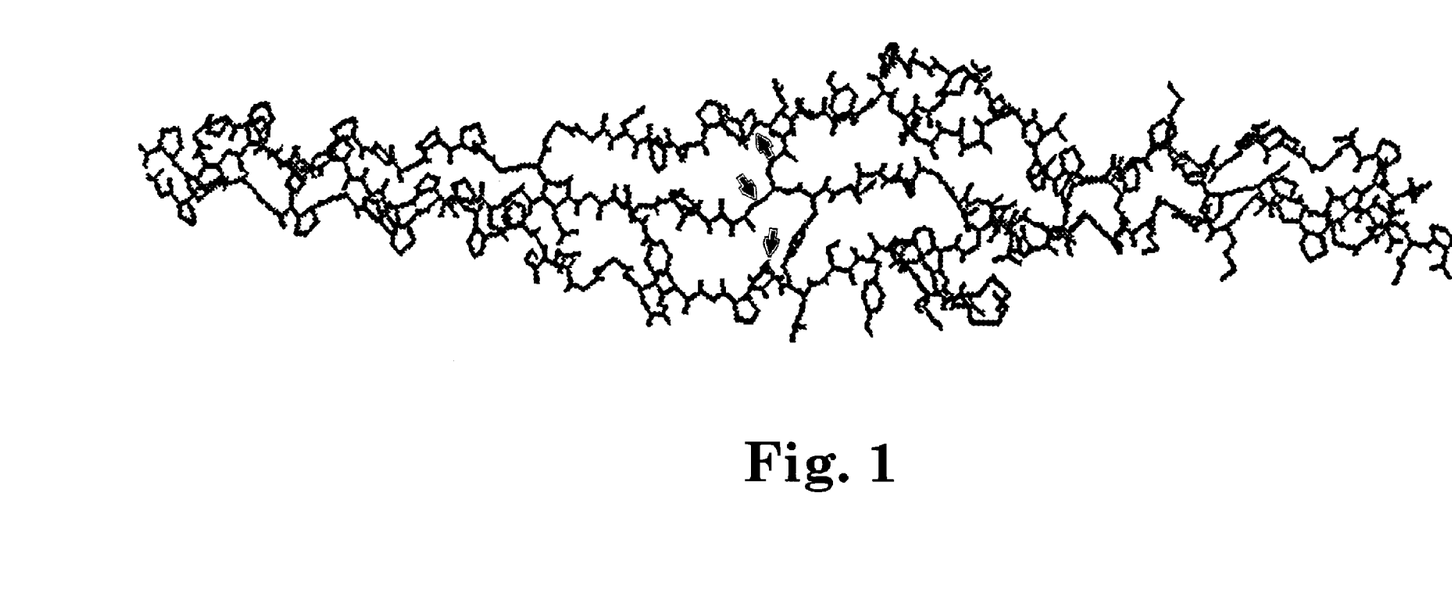
FIG. 1 shows a three-dimensional computer model of the N-terminal propeptide-telopeptide region of human procollagen type I (a triple helix of two α1 chains and one α2 chain). The structure was produced on a Silicon Graphics workstation using Biosym software. The energy-minimized structure is produced after manual chain pull-ins to speed the process of computing the energy minimums. Points of cleavage with N-pro-peptidase are marked with a "▼".
Figure 2:
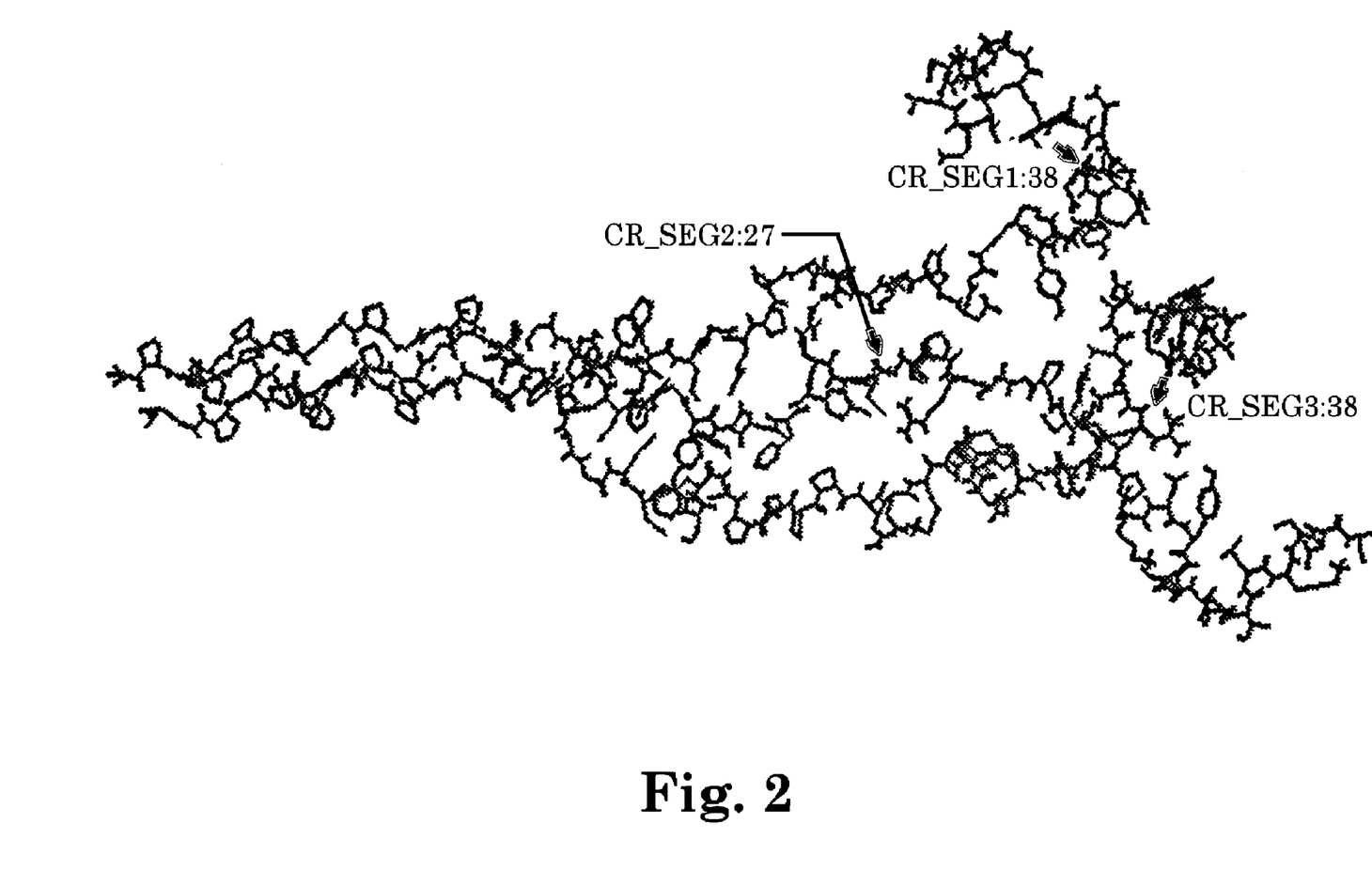
FIG. 2 shows a three-dimensional computer model of the C-terminal propeptide-telopeptide region of human procollagen type I (a triple helix of two α1 chains and one α2 chain). The structure was produced on a Silicon Graphics workstation using Biosym software. The energy-minimized structure is produced after manual chain pull-ins to speed the process of computing the energy minimums. Points of cleavage of the extra-helical peptide from the C-terminal pro-region are marked with a "▼". In the two α1 chains, this is before Gly 38; in the α2 chain, it is before Glu 27.

In a preferred embodiment, construct design is effected by first preparing a three-dimensional model of a procollagen helix at the propeptide-telopeptide junction, then introducing amino acid substitutions that would allow cleavage with specific proteolytic enzymes. For example, FIGS. 1 and 2 depict the structures of the N- and C-terminal propeptide-telopeptide regions of human type I procollagen, respectively. The structures are energy-minimized and the native cleavage sites are marked. Molecular modeling is performed to ensure that the substitutions do not disrupt the folding of this region so as to inhibit processing, secretion, helical formation, or site-specific proteolytic agent accessibility.

Molecular constructs are then generated by either mutating procollagen-encoding cDNAs or splicing nucleic acids encoding the selected collagen chain with nucleic acids encoding the selected site-specific proteolytic agent recognition site. Mutation may be effected by site-directed mutagenesis, nucleotide insertion or substitution (e.g., by PCR-based mutagenesis) or replacement of oligonucleotides by cloning. The insertion site is preferably at or within 100, preferably within 30, more preferably within 10, nucleotides distal to the procollagen site-specific proteolytic agent cleavage site encoding sequence. The substituted nucleotides are within 60, preferably within 36, preferably within 18, nucleotides distal to the procollagen site-specific proteolytic agent cleave site encoding sequence. Preferred constructs additionally comprise nucleic acids including a promoter region necessary for the expression of the encoded procollagen in an appropriate host. Preferred promoters that are constitutive in cultured cells include cytomegalovirus (CMV), simian virus (SV), and Rous sarcoma virus (RSV) promoters. Preferred promoters for tissue-specific expression (e.g., in mammary gland cells) of transgenic animals include casein or acid whey protein promoters. Preferred promoters for expression in yeast include phosphoglycerol kinase (PGK), alcohol dehydrogenase (ADH), and galactose (GAL).

The construct is then transfected into and expressed in a cellular expression system, preferably an expression system wherein the mutated procollagen is secreted. In less preferred embodiments, the recombinant PROcollagen is not sufficiently secreted, and recovery entails lysing the cells and centrifuging the lysate to remove cellular debris. In one embodiment, the cells are selected or engineered to express both the recombinant procollagen and a site-specific proteolytic agent capable of specifically cleaving the procollagen at the recognition site. Alternatively, the appropriate site-specific proteolytic agents are introduced in an amount sufficient to cleave the propeptides from the procollagen molecules prior to fibriliogenesis in the processing steps.

Collagen chains are purified from the medium by methods known in the art. See, for example, Miller and Rhodes, *Methods in Enzymology* (1982) 82:33–64, or Sage and Bernstein, *Methods in Enzymology* (1982) 82:96–127. Resulting collagen compositions may be sterilized, for example, by passage through 0.2 $\mu$m filters (e.g., Millipore filters). Sterility may be confirmed by, for example, culturing aliquots on nutrient agar for at least 72 hours at 25 and 37° C. For therapeutic uses, it is desirable to ensure the non-toxicity, biocompatibility, and non-immunogenicity of the resulting recombinant collagen compositions. For example, non-immunogenicity in humans is confirmed by dermal sensitivity testing.

The invention provides a wide variety of applications of the subject recombinant procollagens and collagens in tissue and cell culture and therapy. For example, the subject procollagens and collagens are used to promote adhesion and growth of cells on a wide variety of solid substrates in various forms, such as slides, filaments, sheets, plates, flasks, bottles, fibers, etc., and compositions such as plastics, glass, metals, saccharide-based polymers, etc. The collagens provide a wide range of therapeutic applications, such as use in biodegradable sutures, synthetic dermal skin, biodegradable hemostatic sponges, tissue augmentation (including modifying localized soft tissue appearance), etc.

Tissue augmentation using collagen compositions has been thoroughly studied, documented, and implemented in widespread clinical settings. See, for example, DeLustro et al., *J. Biomed. Mater. Res.* (1986) 20:109–120; Elson, *J. Dermatol. Surg. Oncol.* (1989) 15:301–303; Elson, *Am. J. Cosmetic Surg.* (1992) 9:267–271; Klein et al., *J. Dermatol. Surg. Oncol.* (1985) 11:337–339; Klein et al., *Geriatric Dermatology: Clinical Diagnosis and Practical Therapy*, Chapter 8, pp. 47–49, Igaku-Shoin (publ), NY (1989); Kligman, *J. Dermatol. Surg. Oncol.* (1988) 14 (suppl I):35–38; Kligman et al., *J. Dermatol. Surg. Oncol.* (1986) 12:351–357; Kligman et al., *J. Dermatol. Surg. Oncol.* (1988) 14 (suppl I): 10–12; Knapp et al., *Plas. Reconstr. Surg.* (1977) 60:398–405; Knapp et al., *J. Surg. Res.* (1977) 23:96–105; Varnavides et al., *Br. J. Dermatol.* (1987) 116:199–206; etc.

EXAMPLES

The following examples are offered by way of illustration and not by way of limitation.

Example 1

Three-Dimensional Computer Modeling of Single Site-specific Protease Recognition Site Insertion Three-dimensional models for the N- and C-terminal propeptide-telopeptide regions were performed as outlined above. FIGS. 1 and 2 depict the energy-minimized structures of the N- and C-terminal propeptide-telopeptide regions of human type I procollagen, respectively. Substitutions were then inserted at the N-terminal cleavage junction site to generate a non-natural site-specific proteolytic agent recognition site and new models prepared to determine their effects on collagen folding.

Figure 3:
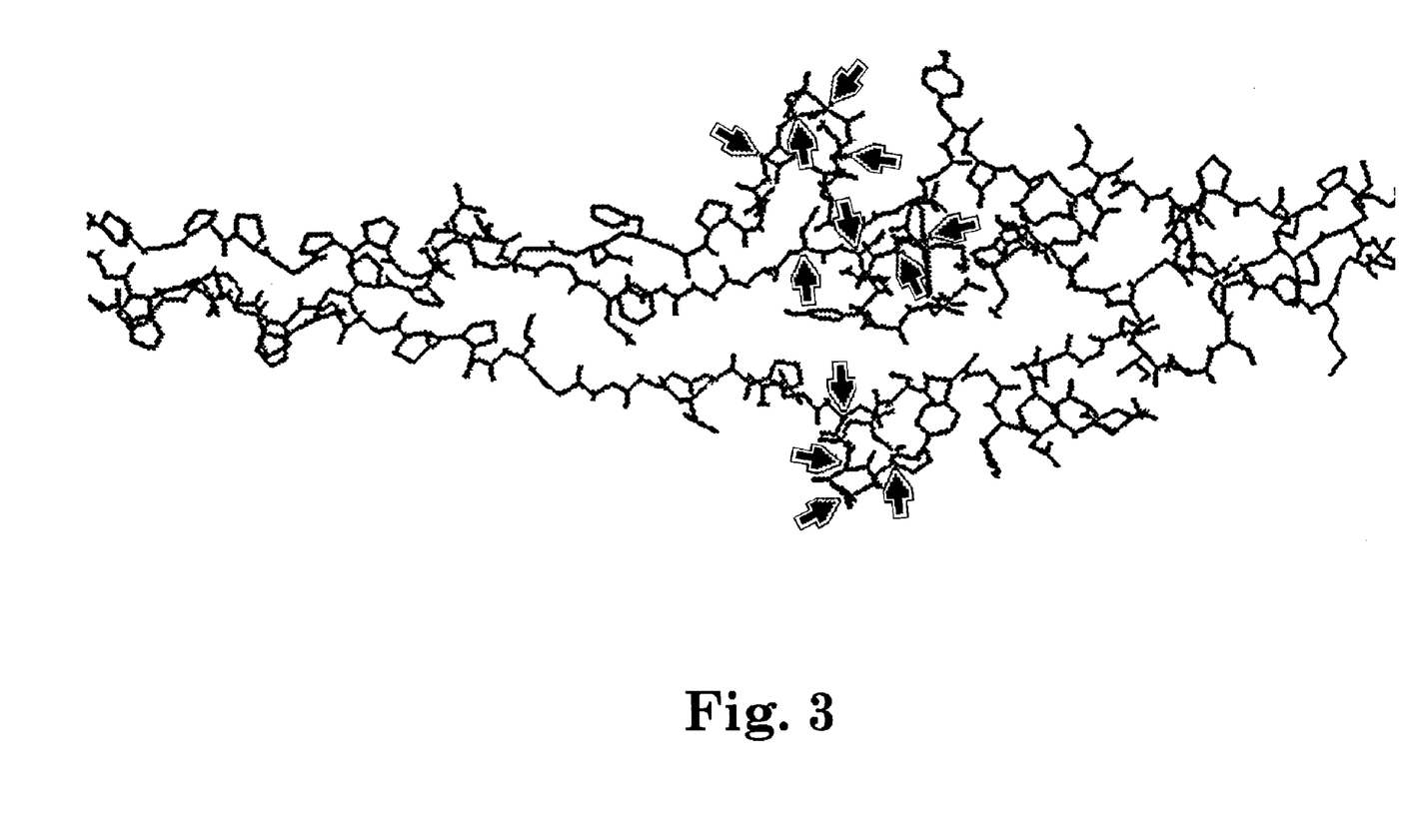
FIG. 3 shows a three-dimensional computer model of the N-terminal propeptide-telopeptide region of a mutant human procollagen type I containing the DDDK insertion. The structure was produced on a Silicon Graphics workstation using Biosym software. The energy-minimized structure is produced after manual chain pull-ins to speed the process of computing the energy minimums. The insertional loop members are marked with a "▼".
Figure 4:
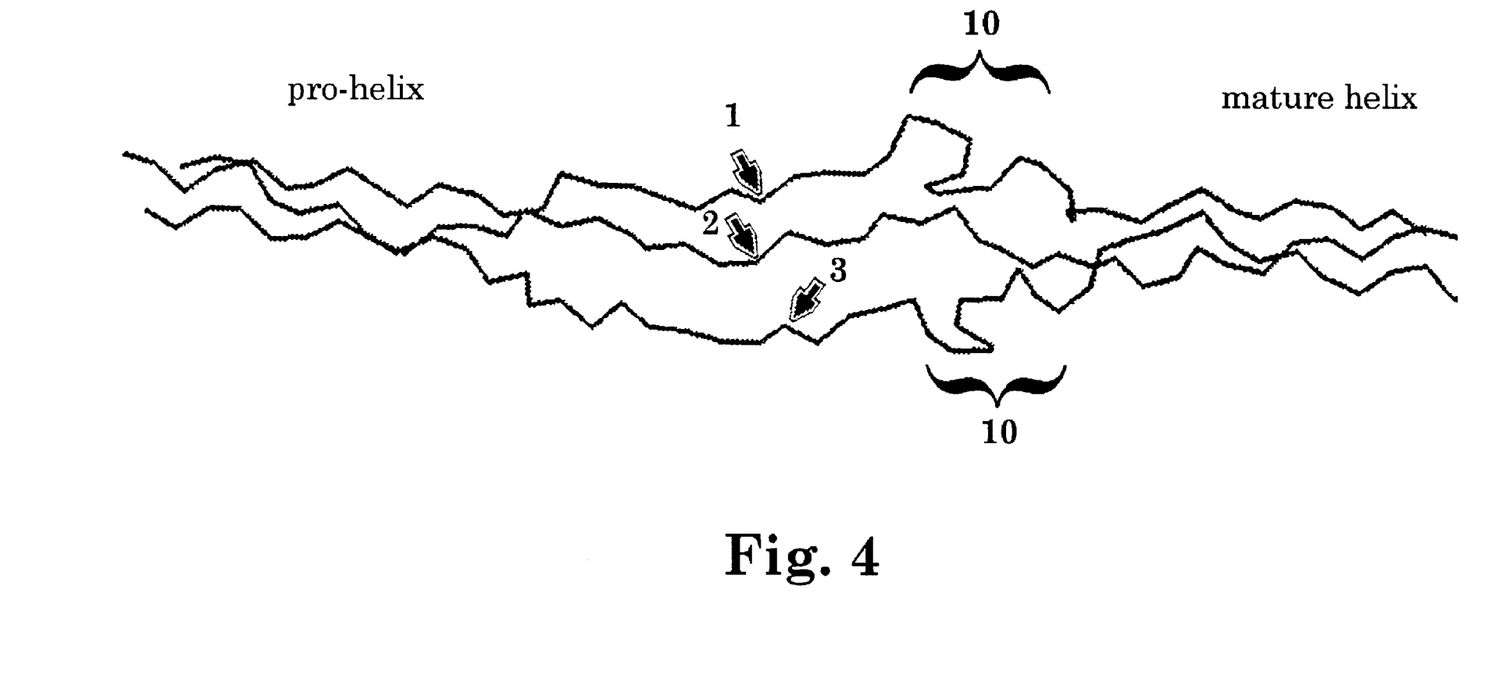
FIG. 4 shows the proteolytic cleavage site of the mutant human procollagen type I containing the DDDK insertion. Points of cleavage of N-propeptidase are marked with a "▼". Regions in which the α1 chains are "coiled" are designated with a "10".

FIG. 3 depicts an N-terminal fragment containing a DDDK (SEQ ID NO:1:) insertion in all three chains, introducing a recognition and cleavage site for enterokinase into the propeptide-telopeptide junction region. As shown in FIG. 4, the proteolytic cleavage site of this mutant is particularly accessible in the energy-minimized structure.

Example 2

Generation of Molecular Constructs for Recombinant Human Procollagens

A. cDNA Clones Encoding Human α1(I) and α2(I) Procollagens

A cDNA clone containing the entire coding region of human α1(I) procollagen is obtained from the Whitehead Institute (Cambridge, Mass.). The description of the cDNA is described in Stacey et al., *J. Virol.* (1987) 61:2549. The nucleotide sequence of this clone (pHUC) is described in Tromp et al., *Biochem. J.* (1988) 253:919, and also under Accession No. X07884 (Genbank, Los Alamos, N.M.). A cDNA clone (pSTL14) containing the entire coding region of human α2(I) procollagen is described in Lee et al., *J. Biol. Chem.* (1988) 263:13414. The nucleotide sequence of human α2(I) procollagen is listed under Accession No. J03464 (Genbank), and the numbering system used assigns nt 1 to the transcription start point, according to Dickson et al., *Nuc. Acids Res.* (1985) 13:3427.

B. Introduction of Cleavage Site Into the Junction of N-Propeptide and N-Telopeptide of the Human α1(I) Procollagen cDNA A specialized cloning vector (pPL1) is created by isolating the AflIII/SspI region of Bluescript II KSM13+ from nucleotide position 1153 to 2850 (Stratagene Cloning Systems, La Jolla, Calif.) and inserting a double-stranded deoxyoligonucleotide polylinker containing the restriction sites (in order) HindIII, PvuII, DraIII, and BamHI. Using pHUC as a template, a 618 nt region of the 5' end of the cDNA is amplified by the Polymerase Chain Reaction (Perkin Elmer Cetus, Norwalk, Conn., according to the manufacturer's instructions) using the oligodeoxynucleotide primer #1 ACGCCAAGCTTGGCTGCAGGTCGA (SEQ ID NO:22:) and primer #2 pCTG TTTATCATCGTCGGGAGCAAAGTTTCCTCC (SEQ ID NO:23:). The underlined nucleotide sequence in primer #2 codes for the amino acid recognition site DDDK (SEQ ID NO:1:) for the proteolytic enzyme enterokinase. The 610 nt DNA fragment generated by the PCR reaction is cleaved with the restriction enzyme HindIII, and cloned into pPL1 at the HindIII/PvuII sites, creating pPL1-1. Next, the PvuII/DraIII fragment from the human α1(I) procollagen cDNA (nt 858 to nt 1797) is cloned into pPL1-1 at the PvuII/DraIII sites, creating pPL1-2. The next step is to insert the PvuII/PvuII (nt 569 to nt 858) fragment of the human α1(I) procollagen cDNA into pPL1-2 at the PvuII site, creating pPL1-3. This PvuII/PvuII fragment inserts itself into the vector in either orientation, so clones which contain the orientation identical to the human α1(I) procollagen cDNA are identified by DNA sequence analysis following the manufacturer's protocol (using Sequenase™ DNA sequencing kit by U.S. Biochemicals, Cleveland, Ohio, and the deoxynucleotide GAGTCACCCACCGAC CAAGA (SEQ ID NO:24:) as the primer). The cDNA fragment from the human α1(I) procollagen cDNA from the DraIII site at position 1797 to the BamHI site at position 2886 is cloned into pPL1-3 at the DraIII/BamHI site, creating pPL1-4. The product of these steps is the continuous region of the human α1(I) procollagen cDNA from the 5' end of the cDNA to the BamHI site at position 2886 with the introduction of a coding region for the amino acids DDDK, which is the amino acid recognition site for enterokinase.

C. Introduction of Cleavage Site Into the Junction of C-Telopeptide and C-Propeptide of the Human α1(I) Procollagen cDNA Another specialized cloning vector (pPL2) is created by following the procedure described above, but using a polylinker which contains the recognition sites for the restriction enzymes (in order) SalI, HindIII, BamHI, BspEII, and SspI. First, a fragment of the human α1(I) procollagen cDNA from the BamHI site at position 2886 to the BspEI site at position 3817 is cloned into the vector at the BamHI/BspEI site, creating pPL2-1. pPL2-1 is digested with the restriction enzymes Eco47III and XhoI, and the 106 bp fragment is discarded. A double-stranded deoxyoligonucleotide with the sequence GCTGGTTTCGACTRCAGCT-TCCT CCC CCAGCCACCTCAAGAGAAGGCTCAC-GATGGTGGCCGCTACTACCGGGCT <u>TGG</u>GATGATGCCAATGTGGTTCGTGACCGTGACC (SEQ ID NO:25:) is inserted into pPL2-1 at the Eco47III/XhoI site, creating pPL2-2. This double-stranded deoxyoligonucleotide contains three additional (underlined) deoxynucleotides (as compared to the human α1(I) procollagen cDNA in this region) which code for the amino acid tryptophan. Next, a fragment of the human α1(I) procollagen cDNA from nt 3818 to 4611 is removed by the restriction enzymes BspEI and SspI and inserted into pPL2-2 at the BspEI/SspI site, creating pPL2-3.

D. Assembly of Human α1(I) Procollagen cDNA With Non-Natural Cleavage Sites at the Propeptide-telopeptide Junctions The human α1(I) procollagen cDNA containing additional nucleotide sequences within the cDNA, which code for additional amino acid(s) at the N-terminal propeptide-telopeptide and C-terminal telopeptide-propeptide junctions, is created by removal of the HindIII/BamHI fragment from pPL1-4 containing the 5' region of the human α1(I) procollagen cDNA, as described in section B above, and inserting this fragment into the HindIII/BamHI sites of pPL2-3 containing the 3' region of the human α1(I) procollagen cDNA, creating pM α1(I). This results in an α1(I) procollagen cDNA that codes for a polypeptide which can be cleaved at the N-terminal propeptide-telopeptide junction with enterokinase, leaving no additional terminal amino acids, and at the C-terminal telopeptide-propeptide with N-chlorosuccinimide, leaving the terminal amino acid tryptophan, according to the method described in Saito et al., *J. Biochem.* (1987) 101:123.

E. Use of Heterologous N-Propeptide and Introduction of Cleavage Site Into the Junction of N-Propeptide and N-Telopeptide of the Human α2(I) Procollagen cDNA A specialized cloning vector (pPL3) is created as described in section B, but using a polylinker which contains the restriction sites (in order) SalI, SphI, PmlI, MscI, and Sse8387I. The human α2(I) procollagen cDNA is excised from pSTL14 using SphI and SmaI restriction enzymes. The resulting DNA fragment is treated with T4 DNA polymerase in the presence of deoxynucleotides to make a blunt end at the 5' end of the cDNA. This fragment is subcloned into the Bluescript II vector at the EcoRV and SmaI sites. The α2(I) procollagen cDNA fragment inserts itself into the vector in either orientation, so clones in which the SmaI site is reconstituted are selected and given the name of pα2(I). Polymerase Chain Reaction is performed according to the manufacturer's instructions (Perkin Elmer Cetus, Norwalk, Conn.) using *Saccharomyces cerevisiae* genomic DNA as template and the phosphorylated deoxyoligonucleotides pGTGGTATGCAAATTTTTGTCAAGACTTTGACTG (SEQ ID NO:26:) and pCCACCTCTCAATCTCAAGACT (SEQ ID NO:27:) as primers to isolate a fragment of the yeast gene UBI1 (ubiquitin) described in Oezkaynak et al., *EMBO J.* 6:1429, and listed under Accession No. X05728 (Genbank). The 232 bp DNA fragment is subcloned into the vector at the PmlI/MscI site, creating pPL3-1. This fragment inserts itself into the vector in either orientation, such that clones which contain the orientation identical to that of the human α2(I) procollagen cDNA are identified by digestion with the restriction enzymes PmlI and MscI. A second PCR reaction is performed using pα2(I) DNA as the template and the two deoxyoligonucleotides pCCAGTATGATGGAAAA GGAGTT (SEQ ID NO:28:) and CGAGCACCTGCAG-GACCAGTT (SEQ ID NO:29:) as the primers for this reaction. The 159 bp DNA fragment is digested with Sse8387I and subcloned into pPL3-1 at the MscI/Sse8387I sites, creating pPL3-2. pα2(I) is digested with SalI and PmlI, and the 199 nt fragment is isolated and inserted into pPL3-2 at the SalI and PmlI sites, creating pPL3-3. pα2(I) is digested with SalI and Sse8387I, and the 475 bp fragment is discarded. pPL3-3 is digested with SalI and Sse8387I, and the 600 bp DNA fragment is isolated and cloned into pα2(I) at the SalI and Sse8387I sites, creating pPL3-4. This creates human α2(I) procollagen cDNA which contains the endogenous signal sequence, but codes for the yeast ubiquitin polypeptide, which replaces the endogenous N-propeptide. The human α2(I) procollagen can be cleaved at the N-propeptide-N-telopeptide junction with a ubiquitin-specific processing protease, as described in Tobias and Varshavsky, *J. Biol. Chem.* (1991) 266:12021.

F. Use of Heterologous C-Propeptide and Introduction of Cleavage Site Into the Junction of C-Telopeptide and C-Propeptide of the Human α2(I) Procollagen cDNA pα2(I) is digested with AvrII and EcoRI, and the 909 bp DNA fragment is discarded. Next, Polymerase Chain Reaction s performed according to the manufacturer's instructions using pα2(I) as template and the deoxyoligonucleotides TGGTCCTAGGGGCCCTGCTGG TCCTT (SEQ ID NO:30:) and pTCTACCTTCTATAGCCCTGTAGAAGTCTCCATCGTA (SEQ ID NO:31:) as primers. The underlined nucleotide sequence in the second primer codes for the amino acid recognition site (IEGR) (SEQ ID NO:02:) for Factor $X_a$. A DNA product of 220 bp is isolated and then digested with AvrII. A second PCR reaction is performed using RT-PCR according to the manufacturer's instructions (Perkin Elmer Cetus, Norwalk, Conn.), using as template total RNA isolated from mouse spleen by the procedure of Han et al., Biochem. (1987) 26:1617. Random hexamers are used as primers for the reverse transcription of mouse RNA. The two PCR primers in the PCR reaction are pAAACAGAAG-CACCAGTC GGTATTCA (SEQ ID NO:32:) and ATAT-GAATTCTCAGGTGCACGCACAGGTTGGCCG TA (SEQ ID NO:33:). A DNA product of 215 bp which encodes the C-terminus of mouse complement C1q-C subunit (see Petry et al., *Eur. J. Biochem.* (1992) 209:129 and Genbank Accession No. X66295) is isolated and digested with EcoRI. The two digested PCR products are ligated into pα2(I) previously digested with AvrII and EcoRI, as described above, creating pPL4-1. These steps create a human α2(I) procollagen cDNA having the mouse complement C1q-C subunit C-terminus, which replaces the human α2(I) procollagen C-propeptide and introduces a IEGR (SEQ ID NO:2:) recognition site for the protease Factor $X_a$ at the junction of the C-telopeptide and C-propeptide.

G. Assembly of Human α2(I) Procollagen cDNA With Non-Natural Propeptide Domains and Non-Natural Cleavage Sites at the Propeptide-telopeptide Junctions The human α2(I) procollagen cDNA containing ubiquitin in place of the endogenous N-propeptide and the C-terminus of complement C1q-C subunit instead of the endogenous C-propeptide is created by removing the 2850 bp XhoI/XhoI fragment from pPL3-4 (described in section E), inserting this DNA fragment into pPL4-1 (described in Section F) digested with XhoI, and discarding the 2725 bp fragment, creating pM α2(I). The XhoI fragment from pPL3-4 can insert itself into pPL4-1 in either orientation. The orientation which places the translation start codon toward the 5' end of the construction is selected using DNA sequence analysis. This results in α2(I) procollagen cDNA which can be cleaved at the N-terminal propeptide-telopeptide junction with ubiquitin specific processing protease, and at the C-terminal telopeptide-propeptide junction with Factor $X_a$, leaving the terminal amino acids IEGR (SEQ ID NO:2:).

Example 3

Production of Recombinant Human Collagen pSV-SPORT1 (Life Technologies, Ind., Gaithersburg, Md.) is used as the expression vector for the mutated α1(I) procollagen cDNA (pM α1(I) from Example 2D) and the mutated α2(I) procollagen cDNA (pM α2(I) from Example 2G). pSV-SPORT1 is digested with the restriction enzymes SalI and SspI. The fragment containing the mutated α1(I) procollagen cDNA is ligated into pSV-SPORT1 at the SalI and SnaBI sites, creating PSV-M α1(I). pM α2(I) is digested with SalI and SmaI. The fragment containing the mutated α2(I) procollagen is ligated into pSV-SPORT1 at the SalI and SnaBI sites, creating pSV-M α2(I).

Either pSV-M α1(I) or pSV-M α2(I) is co-transfected with pRSV neo into HT1080 cells (American Type Culture Collection, Rockville, Md.) using Lipofectamine Reagent (Life Technologies, Gaithersburg, Md.) and following the manufacturer's protocol for stable transfection of adherent cells. The mutated procollagen product from HT1080 cells transfected with either pSV-M α1(I) or pSV-M α2(I) is secreted into the medium as homotrimeric molecules. After 24 hours, the medium is collected and protease inhibitors are added to a final concentration of 10 mM N-ethylmaleimide, 1 mM PMSF, and 25 mM EDTA. Ammonium sulfate is added to the medium to a final concentration of 30%, and the medium is stored at 4° C. for 16 hours. The medium is centrifuged at 4000 rpm for 10 minutes at 4° C. The pellet is resuspended in 50 mM Tris, pH 7.4, 150 mM NaCl, and protease inhibitors at the concentrations listed above, or in the appropriate buffer for cleavage of one or both of the propeptides from the collagen molecule. See the following sources for specific cleavage agents and reaction conditions: for enterokinase, Sigma Chemical Company, St. Louis, Mo.; for tryptophan chemical cleavage, Saito et al., *J. Biochem.* (1987) 101:123–134; for ubiquitin specific processing enzyme, Tobias and Varshavsky, *J. Biol. Chem.* (1991) 266:12021; for Factor $X_a$, New England Biolabs, Beverly, Mass.

Example 4

Use of Recombinant Human Collagen in Soft Tissue Augmentation

Recombinant human collagen produced as described in Example 3 is adjusted to a collagen concentration of 10 mg/ml by addition of 0.13 M phosphate buffer at pH 7.2 under conditions favoring fiber formation. The resulting suspension of fibrillar collagen is centrifuged at 10,000×g to concentrate the collagen, which is subsequently rediluted to a concentration of 35 mg/ml by the addition of phosphate buffer. The resulting fibrillar collagen suspension is aliquotted into syringes for use in soft tissue augmentation.

A physician attaches a 25-gauge or smaller needle to a syringe containing the recombinant human fibrillar collagen suspension prepared as described above. After attaching the needle to the collagen-containing syringe, the physician injects the collagen subcutaneously into the dermis, using multiple serial punctures, to soft tissue sites in need of augmentation, such as acne scars and wrinkles. Collagen is injected to a particular soft tissue site until the previously depressed area is even with the surface of the surrounding normal skin.

Example 5

Cultureware Coating Assay: Human Dermal Fibroblast Contraction Assay

Recombinant human collagens are assayed and compared with purified human placental, bovine hide, and rat tail collagens for their ability to support gel contraction by human dermal fibroblasts. Recombinant human collagens are prepared as described in Example 3. Human collagen is purified from human placenta by extraction with 0.1 M acetic acid, followed by precipitation of type I collagen by the addition of 1 M NaCl. Bovine hide and rat tail collagens are commercially obtained in soluble form (e.g., Vitrogen).

Primary human dermal fibroblasts obtained from American Type Tissue Culture Collection are suspended in DMEM containing 10% (v/v) fetal calf serum at $1.0–1.4\times10^5$ cells/ml. One (1) milliliter of cell suspension and 2 ml of the same culture medium are added to 1 ml of recombinant collagen at a concentration of 2.5 mg/ml in 10 mM acetic acid. The cell suspension-collagen solution is poured into a 35-mm polystyrene petri dish (Costar) and incubated in a 37° C. tissue culture incubator in 5% $CO_2$ for 5 days to allow contraction to occur.

Rates of contraction are measured each day by placing the culture dish containing the contracted cell matrix over a template containing circles of varying diameter, then estimating the diameter of the contracted cell matrix by comparison with the circles on the template. Recombinant human collagens prepared as described in Example 2 are shown to promote fibroblast contraction at rates at least comparable to those obtained using rat tail, purified human placental, and bovine hide collagens.

All publications and patent applications cited in this specification are herein incorporated by reference, as if each individual publication or patent application were specifically and individually indicated to be incorporated by reference. Although the foregoing invention has been described in some detail by way of illustration and example for purposes of clarity of understanding, it will be readily apparent to those of ordinary skill in the art, in light of the teachings of this invention, that certain changes and modifications may be made thereto without departing from the spirit or scope of the appended claims.

What is claimed is:

1. A recombinant procollagen polypeptide chain comprising a natural collagen polypeptide chain, a first natural procollagen C-terminal propeptide, and a first non-natural site-specific proteolytic agent recognition site, wherein said first non-natural site-specific proteolytic agent recognition site is located between said collagen chain and said first propeptide, and further comprising a second propeptide and a second non-natural site-specific proteolytic agent recognition site, wherein said second non-natural site-specific proteolytic agent recognition site is located between said collagen chain and said second propeptide.

2. A recombinant procollagen chain according to claim 1, wherein said first and said second non-natural site-specific proteolytic agent recognition sites are different.

* * * * *